United States Patent [19]

Miller

[11] Patent Number: 5,680,933
[45] Date of Patent: Oct. 28, 1997

[54] COMBINATION SHOWER CADDY AND ORAL HYGIENE APPLIANCE HOLDER

[76] Inventor: Michael J. Miller, 5715 S. Lake Shore Dr., Shreveport, La. 71119

[21] Appl. No.: 636,224

[22] Filed: Apr. 23, 1996

[51] Int. Cl.[6] .................................................. A45D 40/00
[52] U.S. Cl. ........................ 206/581; 132/309; 206/63.5; 206/229; 206/235; 206/362.2
[58] Field of Search ........................... 132/308–310; 206/63.5, 77.1, 209.1, 228, 229, 235, 361, 362.1, 362.2, 362.3, 581, 823; 200/335; 312/245, 248

[56] References Cited

U.S. PATENT DOCUMENTS

| | | | |
|---|---|---|---|
| D. 251,522 | 4/1979 | Chapman | D6/91 |
| D. 286,599 | 11/1986 | Sussman | D6/525 |
| D. 309,225 | 7/1990 | Scarbro | D6/525 |
| 3,894,550 | 7/1975 | Eaton | 132/309 |
| 4,121,600 | 10/1978 | Riddick et al. | 206/581 |
| 4,661,716 | 4/1987 | Sorlien | 206/581 |
| 4,934,640 | 6/1990 | Bichon | 206/77.1 |
| 5,014,860 | 5/1991 | Emery | 211/106 |
| 5,033,617 | 7/1991 | Hartwein et al. | 206/209.1 |
| 5,076,423 | 12/1991 | Rossack | 206/63.5 |
| 5,086,916 | 2/1992 | Gray | 206/362.1 |
| 5,095,924 | 3/1992 | Stanfield | 206/581 |
| 5,163,561 | 11/1992 | Fitzgerald | 206/581 |
| 5,215,193 | 6/1993 | Dennis | 206/581 |
| 5,299,683 | 4/1994 | Poole | 206/77.1 |

*Primary Examiner*—Jimmy G. Foster
*Attorney, Agent, or Firm*—John D. Gugliotta; David L. Volk

[57] ABSTRACT

A shower caddy having a steam-proof mirror is provide in combination with several oral hygiene appliance holders, including a toothpaste tray for easy storage or retrieval of standard tubes of toothpaste, a toothbrush holder, and a dental floss dispenser with a lower discharge means for dispensing dental floss to the outside of the caddy.

6 Claims, 3 Drawing Sheets

5,680,933

COMBINATION SHOWER CADDY AND ORAL HYGIENE APPLIANCE HOLDER

BACKGROUND OF THE INVENTION

1. Field of the Invention

The present invention relates generally to shower caddies, and, more particularly, to a shower caddy in combination with a toothpaste tray, a toothbrush holder, and a dental floss holder.

2. Description of the Related Art

As is well-known in the art, many forms of shower caddy are known. For example, in U.S. Pat. No. Des. 251,522 issued in the name of Chapman, as well as U.S. Pat. No. 5,014,860, issued in the name of Emery both disclose a shower caddy adapted for a particular function or particular aesthetic.

The general usefulness of shower caddies have also led to combinations within the related arts for providing additional feature, such as mirrors, soap or shampoo dispensers, or additional compartments. Examples appear in U.S. Pat. No. 5,299,683, issued in the name of Poole, U.S. Pat. No. Des. 309,225, issued in the name of Scarbro, as well as U.S. Pat. No. Des. 286,599, issued in the name of Sussman.

Another problem occurs from the use of various oral hygiene implements. While many grooming and hygiene activities can be accommodated within the space and time constraints of a typical shower if utilizing sufficient organization, the acts of brushing and flossing are typically performed outside such an arena. To attempt to do otherwise, however, would generally be associated with several drawbacks. For example, the inability to juggle tooth paste, tooth brush, and dental floss container while under a stream of water would normally create a deterrent. Moreover, the act of brushing or flossing one's teeth is greatly enhanced when utilized in conjunction with a mirror, and mirrors are not normally available within the shower confines.

Consequently, a need has been felt for providing an apparatus and method which can store and organize toothpaste, a toothbrush, and dental floss, while at the same time providing for easy deployment of such implements.

SUMMARY OF THE INVENTION

It is therefore an object of the present invention to provide an improved shower caddy.

It is a further object of the present invention to provide an improved combination shower caddy and oral hygiene appliance holder.

It is a feature of the present invention to provide a shower caddy for organizing and dispensing oral hygiene implements having a steam-proof, anti-fog type mirror to aid a user in performing routine acts of oral hygiene.

Briefly described according to one embodiment of the present invention, a shower caddy is provide in combination with several oral hygiene appliance holders. A flat, vertically mountable, separable, hinged housing is provided supporting and framing a steam-proof mirror of the type currently generally available. Suction cup wall fasteners are provided along the back of the housing for affixment to a shower wall. A horizontally extended and level toothpaste tray is provided for easy storage or retrieval of standard tubes of toothpaste. A toothbrush holder is further provided for easy storage and deployment of a toothbrush. And, a dental floss dispenser, placeable with the separable hinged housing, is provided with a lower discharge means for dispensing dental floss to the outside of the caddy.

An advantage of the present invention is that good oral hygiene habits are made easy in a clean, time-saving manner.

Further, a preferred embodiment of the present invention stores toothpaste, toothbrushes, and floss away from a sink, thereby eliminating the clutter normally associated with bathroom countertops.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1:
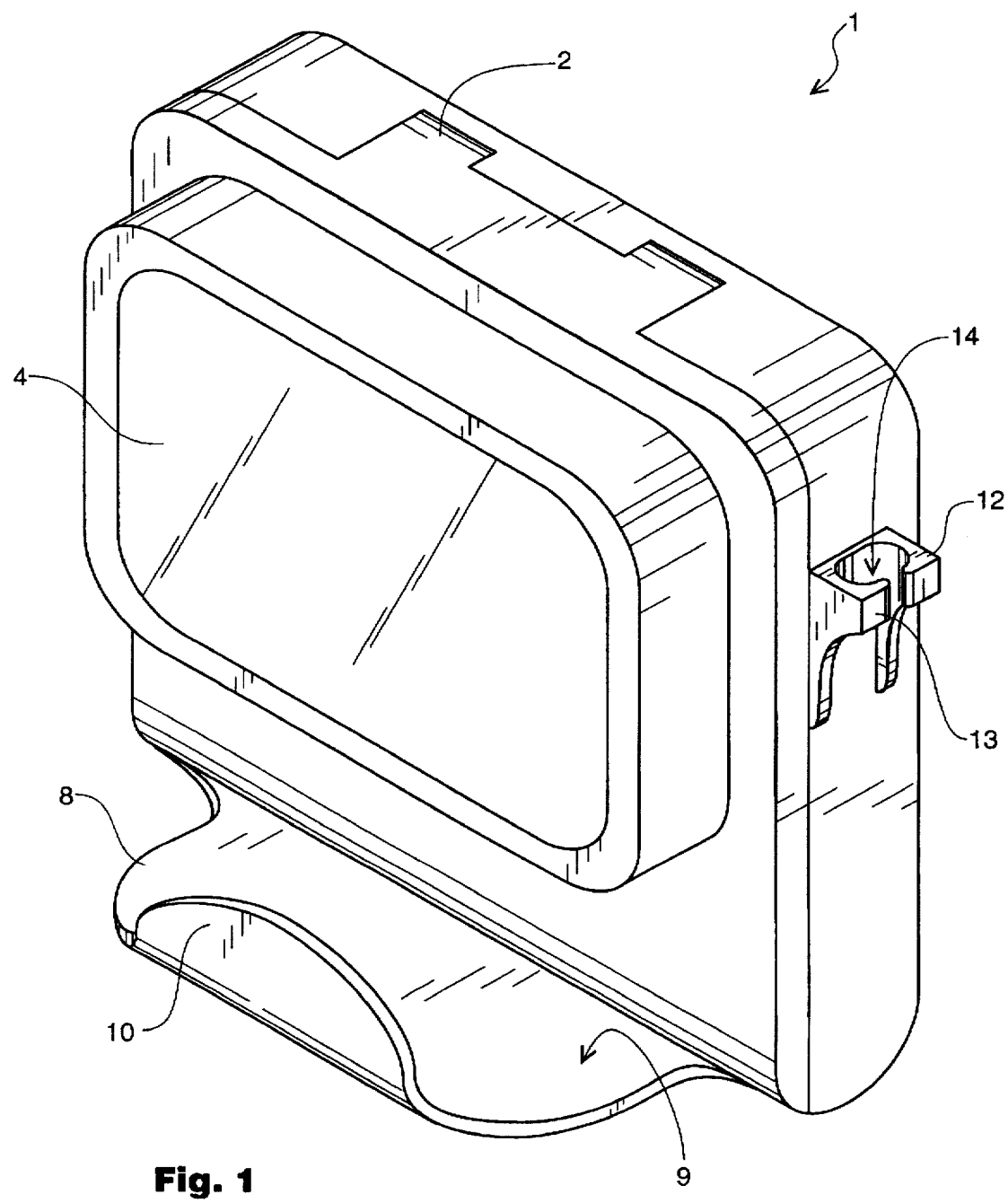
FIG. 1 is a front perspective view of a shower caddy combination according to the preferred embodiment of the present invention.
Figure 2:
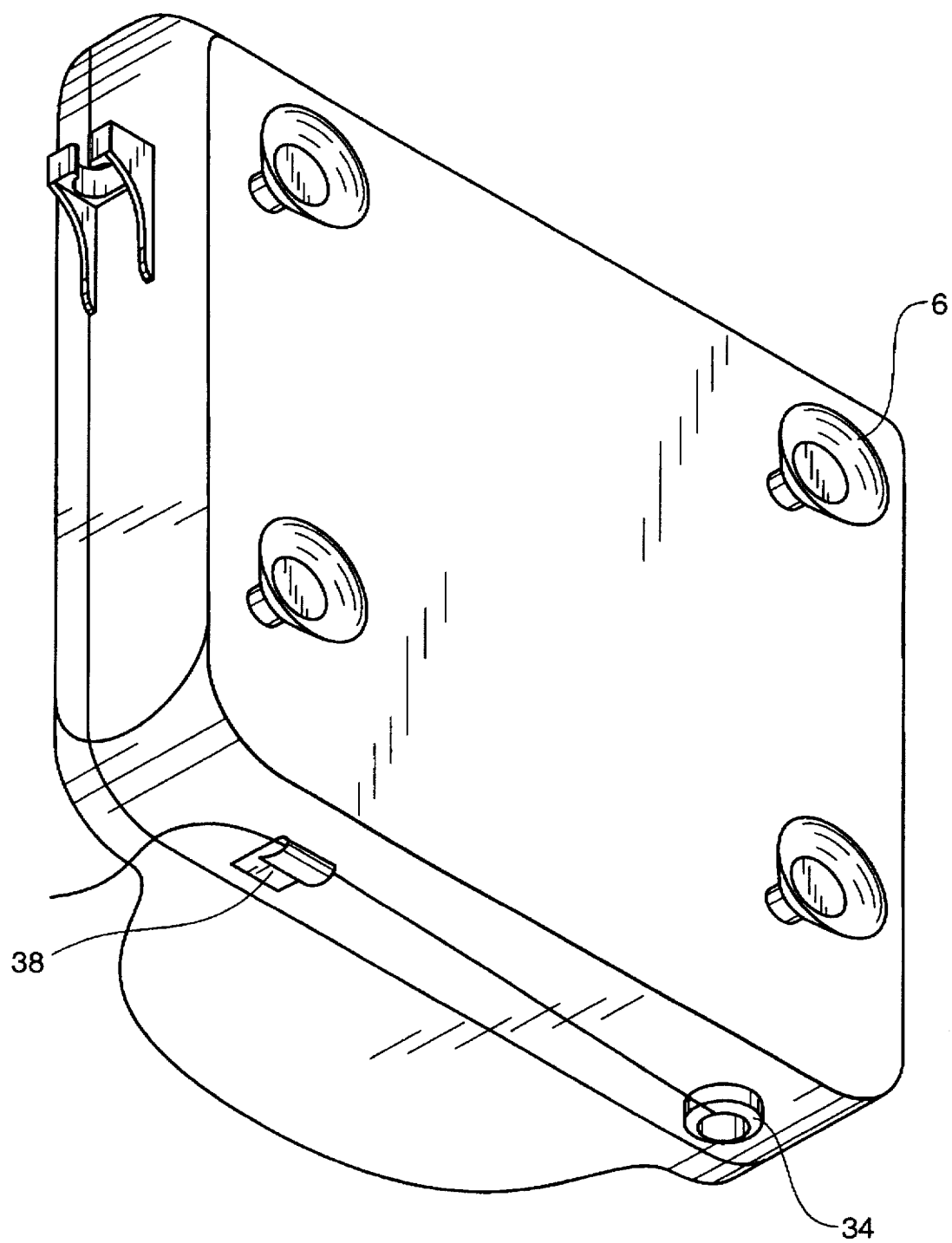
FIG. 2 is a rear perspective view thereof.

Referring now to FIG. 1 and FIG. 2, a shower caddy 1 is shown, according to the present invention, in combination with several oral hygiene appliance holders. A flat, vertically mountable, separable, hinged housing 2 is provided supporting and framing a steam-proof mirror 4 of the type currently generally available. Suction cup wall fasteners 6 are provided along the back of the housing 2 for affixment to a shower wall or other vertical surface, such as a shower door. A horizontally extended and level toothpaste tray 8 is provided for easy storage or retrieval of standard tubes of toothpaste. The toothpaste tray 8 has a horizontal resting surface 9, and terminates in an upwardly curved retaining lip 10. A toothbrush holder 12 is further provided for easy storage and deployment of a toothbrush, and is envisioned as a conventional type having a pair of opposed retaining ears 13 surrounding a holding recess 14.

Figure 3:
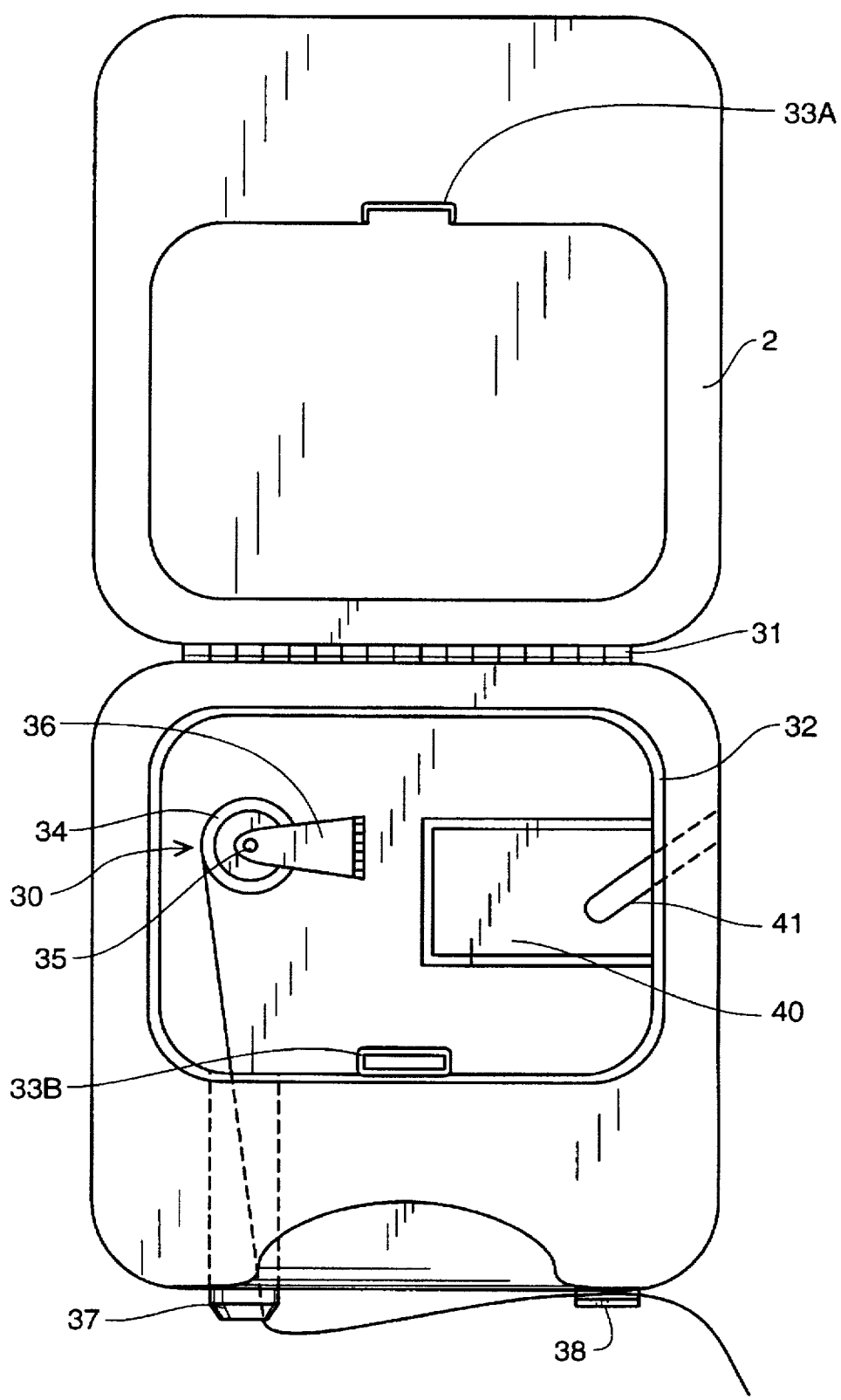
FIG. 3 is a front elevational view thereof shown in an opened configuration.

Referring to FIG. 3, a dental floss dispenser 30 is best shown with the front portion of the housing 2 lifted open about the hinge 31. A sealing O-ring 32 is placed surrounding the opening such as to seal the internal compartment in a water tight fashion when closed. A springed hook 33a impinges against a clasp 33b in order to maintain the housing 2 in a closed condition. A spool of dental floss 34 is mounted upon an axle 35 and held in place by a triangular, swinging retaining arm 36. It is envisioned that the retaining arm 36 is removably affixed to the axle 35 in a snap-type fashion. The dental floss itself is directed downward, exiting the housing 2 through an exit portal 37 which protrudes downwardly slightly in order to make grasping of the dental floss easier. A cutoff blade 38 is provided for removing a selected length of dental floss from the spool 34.

Finally, a storage compartment 40 can also be provided, having a springed door 41. It is felt that this compartment 40 can be effectively utilized to store used and unwanted segments of dental floss temporarily, prior to final disposal.

The foregoing description is included to illustrate the operation of the preferred embodiment and is not meant to limit the scope of the invention. The scope of the invention is to be limited only by the following claims.

What is claimed is:

1. A shower caddy and oral hygiene appliance holder combination comprising:

a flat, vertically mountable, housing, said housing having a front face hinged to a rear section, said rear section having an opening circumscribed by an O-ring type seal for providing a water tight closure when said front face is adjoined with said rear section;

a mirror supported within and framed by said front face;

at least one suction cup wall fastener affixed to said rear section for affixment of said combination to a vertical surface;

a toothpaste tray protruding outwardly from and affixed to said housing;

a toothbrush holder affixed to said housing for providing easy storage and deployment of a toothbrush;

structure forming an opening in said housing;

a dental floss dispenser contained with said housing for dispensing dental floss outward from said combination through the opening.

2. The combination as described in claim 1, wherein said toothpaste tray being horizontally extended and level further comprises:

a horizontal resting surface; and a curved retaining lip terminating said horizontal resting surface in an upwardly curved manner.

3. The combination as described in claim 1, wherein said toothbrush holder comprises:

a pair of opposed retaining ears; and a holding recess surrounded by said retaining ears.

4. The combination as described in claim 1, wherein said mirror is of the anti-fog type proving resistant to fogging and/or steaming.

5. The combination as described in claim 1, wherein said dental floss dispenser comprises:

a spool of dental floss mounted upon an axle, said axle affixed to the rear section of said housing;

a swinging retaining arm for maintaining said spool upon said axle, said retaining arm further being removably affixed to the axle in a snap-type fashion; and a cutoff blade affixed to said housing for removing a selected length of dental floss from the spool.

6. In the combination as described in claim 1, further comprising:

a storage compartment to store used and unwanted segments of dental floss temporarily, prior to final disposal, said storage compartment formed within said housing and accessible to the outside of said housing; and a springed door pivotally closing said storage compartment.

\* \* \* \* \*